(12) United States Patent
Fayet

(10) Patent No.: US 8,192,389 B2
(45) Date of Patent: Jun. 5, 2012

(54) MONOCANALICULONASAL AND/OR MONOCANALICULAR INTUBATION ASSEMBLY, MAINLY FOR NASOLACHRYMAL IMPERFORATION

(76) Inventor: Bruno Fayet, Paris (FR)

( * ) Notice: Subject to any disclaimer, the term of this patent is extended or adjusted under 35 U.S.C. 154(b) by 475 days.

(21) Appl. No.: 12/312,387

(22) PCT Filed: Oct. 26, 2007

(86) PCT No.: PCT/FR2007/001770
§ 371 (c)(1),
(2), (4) Date: Jun. 12, 2009

(87) PCT Pub. No.: WO2008/056060
PCT Pub. Date: May 15, 2008

(65) Prior Publication Data
US 2010/0030126 A1   Feb. 4, 2010

(30) Foreign Application Priority Data
Nov. 8, 2006   (FR) ...................... 06 09736

(51) Int. Cl.
*A61M 5/00* (2006.01)
*A61B 17/00* (2006.01)

(52) U.S. Cl. ................. 604/9; 604/8; 128/887
(58) Field of Classification Search ............ 604/8, 9; 128/887
See application file for complete search history.

(56) References Cited

U.S. PATENT DOCUMENTS

| | | | |
|---|---|---|---|
| 5,417,651 A | 5/1995 | Guena et al. | 604/8 |
| 6,238,363 B1* | 5/2001 | Kurihashi | 604/8 |
| 6,605,108 B2* | 8/2003 | Mendius et al. | 623/1.11 |
| 2002/0151960 A1 | 10/2002 | Mendius et al. | 623/1.15 |
| 2006/0122553 A1* | 6/2006 | Hanna | 604/8 |
| 2010/0274204 A1* | 10/2010 | Rapacki et al. | 604/285 |

FOREIGN PATENT DOCUMENTS

| | | |
|---|---|---|
| EP | 1 048 275 | 11/2000 |
| FR | 2 632 531 | 12/1989 |
| WO | WO 2006/039096 | 4/2006 |

OTHER PUBLICATIONS

International Search Report (3 pages—dated Jun. 30, 2008).

* cited by examiner

*Primary Examiner* — Leslie Deak
(74) *Attorney, Agent, or Firm* — Renner, Kenner, Greive, Bobak, Taylor & Weber

(57) ABSTRACT

Monocanaliculonasal and/or monocanalicular intubation assembly mainly intended for nasolachrymal imperforation, comprising a mandrel (2) made of a first substantially rigid material, such as a metal, and a tube (1) made of a second material that is less rigid than the first material and essentially flexible, such as silicone, a blocking plug (6) for locking the tube in position in the lachrymal duct and protruding laterally from the tube, characterized in that the length of the tube (1) is smaller than the length of the mandrel (2) and the mandrel (2) has a greater thickness, measured in a direction perpendicular to the longitudinal direction, relative to that of the tube (1), such that said mandrel can be inserted inside the tube and withdrawn therefrom.

17 Claims, 1 Drawing Sheet

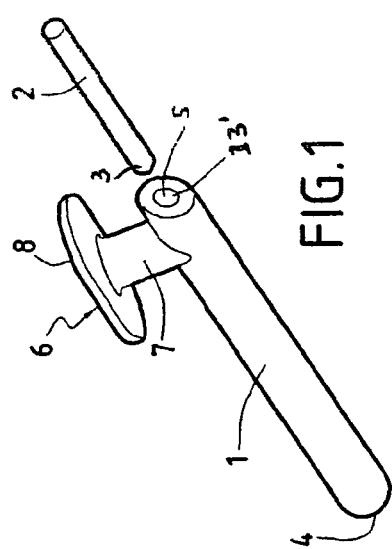
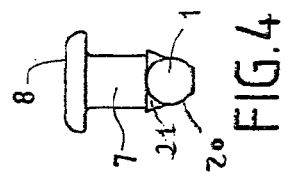
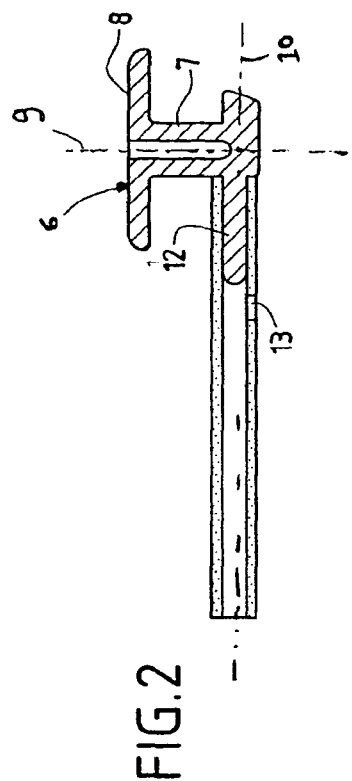
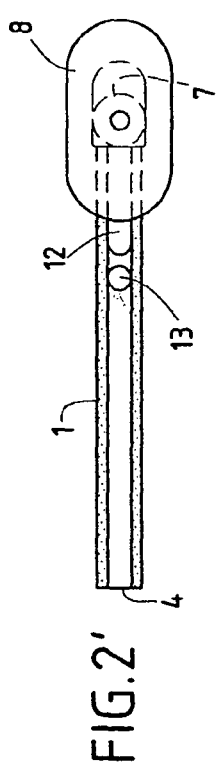
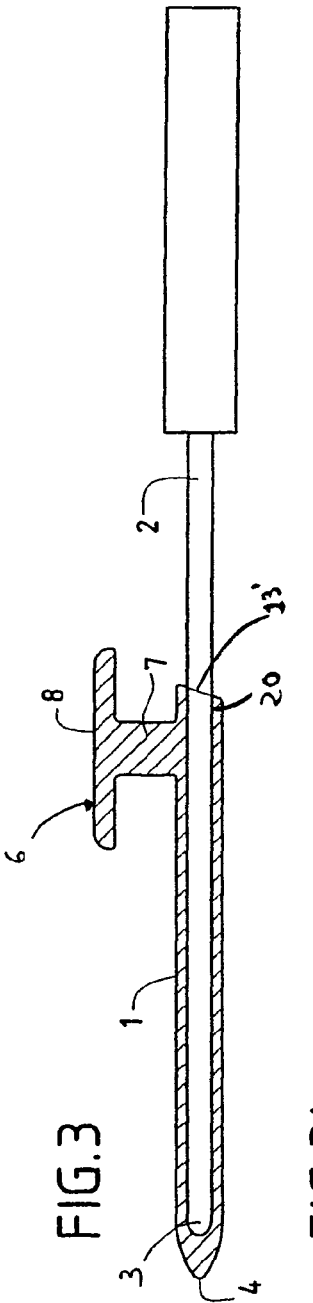
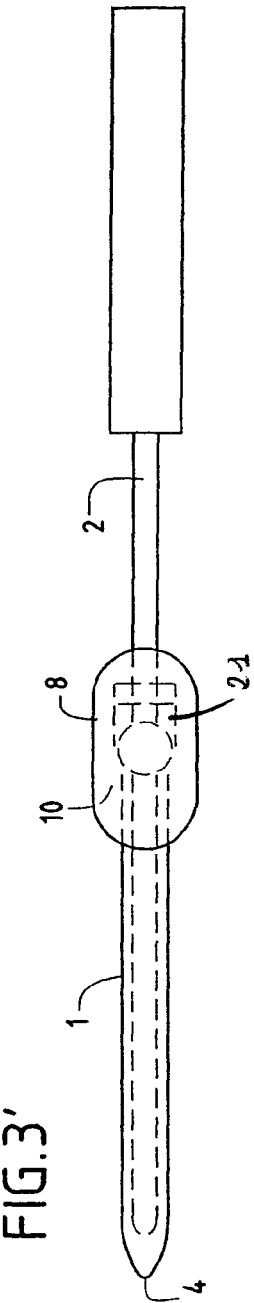

MONOCANALICULONASAL AND/OR MONOCANALICULAR INTUBATION ASSEMBLY, MAINLY FOR NASOLACHRYMAL IMPERFORATION

The present invention relates to a monocaniculonasal and/or monocanalicular intubation assembly mainly intended for nasolachrymal imperforation and to canalicular pathologies.

Monocanalicular assemblies are already known from the prior art which comprise a mandrel made of a substantially rigid material, such as metal, and a tube made of a substantially flexible material, in particular silicone, fixed to one end of the mandrel. At the other end of the silicone tube an anchoring plug is formed, referred to as a metal plug, formed by a shank extending between a collar at one end of the shank and a bulb at the other end of the shank, the bulb being connected to the silicone tube and the shank being substantially perpendicular to the direction of longitudinal extension of the tube.

These known systems are used as follows. The objective is to unblock a blocked lachrymal duct. To achieve this, the monocanalicular assembly is introduced from the side of the eye by the mandrel into the lachrymal duct until it comes into contact with the material blocking the duct, the latter material is then pierced by the mandrel. Then, the metal mandrel ends substantially at the nasal end of the lachrymal duct, whereas the tube, which follows in turn, traverses the material blocking the duct and thus forms a passage through the latter. The following stage consists of removing the metal mandrel by pulling it out through the nose. To achieve this the surgeon has to "root around" in the nose, which can prove to be dangerous, particularly when operating on an infant. A full general anaesthetic is required, particularly in the case of orotracheal intubation or a laryngeal mask.

The present invention is aimed at overcoming the disadvantages of the prior art by proposing a monocanalicular and/or monocanaliculonasal intubation assembly, which allows a surgeon to operate in a more secure manner and, in particular, no longer requires the latter to work on the nose of the patient to extract the mandrel. Thus, in particular, it is no longer necessary, for the application of said monocanicular intubation which passes though an obstruction in the lachrymal or canalicular duct for the purpose of reopening it for the passage of tears, to use a general anaesthetic, particularly a full general anaesthetic, a simple inhalation anaesthetic, without orotracheal intubation is sufficient according to the invention.

According to the invention the monocanalicular and/or monocaniculonasal intubation assembly is as defined in claim 1 or claim 2.

Advantageous refinements are described in the subclaims.

By means of this novel monocanalicular intubation assembly the use is simplified. In fact, now the surgeon can always introduce the assembly from the eye side of the lachrymal duct until, on the one hand, the plug comes into contact with a shoulder formed at the eye side end of the lachrymal duct, to lock the intubation assembly in position, and, on the other hand, the mandrel, surrounded by the tube, has pierced the material obstructing the lachrymal duct or the lachrymal passages to allow the formation of an opening around the silicone tube, which opening will remain once the tube has been removed some time later.

To remove the mandrel, the surgeon no longer has to pass through the nose, which is associated with substantial risks for the patient. According to the invention the surgeon bears on the lachrymal duct with the mandrel or holds the tube with clamps at the duct and simply removes the mandrel from the eye side of the lachrymal duct by pulling. It is no longer removed through the nose as is the case according to the prior art. Furthermore, it is also no longer necessary to pull the assembly up to the end of the silicone tube to move the plug into position. Lastly, once the mandrel has been removed, it is no longer necessary to cut off the tube, as the latter has the desired dimension from the start, which also makes it possible to economise in terms of the manufacturing cost of the monocanalicular intubation assembly, the longitudinal dimension of the silicone tube of which is much shorter than in the prior art.

In particular, the provision of a hole in the bottom lateral part of the surface of the tube makes it possible to prevent the canalicular epithelium being subject to reactional hyperplasia on contact. In fact, in the case of an opening that is not made laterally but at the proximal end of the tube, the hyperplasia would have the tendency to follow all of the contours and interstices and to colonise the hole opening over a certain length. Furthermore, an opening in the form of slot at the side of the bulb respects the latter completely. When the mandrel is removed the slot collapses and there is no colonisation. Lastly, the fact that the bulb remains closes limits the risk of canaliculitis.

The plug is preferably formed by a shank with a collar situated at one free end and a bulb situated at the other tube side end, the shank and the tube extend in two directions which cross one another, in particular perpendicularly.

According to a preferred embodiment of the invention the plug is fixed to one end of the tube by insertion of a tab projecting laterally from the shank of the plug and passing inside the tube against the interior wall of the silicone tube, in particular by tightening adjustment.

According to this same embodiment a hole is formed in the tube substantially close to the plug, to allow the insertion of the mandrel into the tube through the lateral wall of the tube.

According to another preferred embodiment of the invention the plug comes from the lateral surface of the tube and in particular is moulded in one piece with the latter and the mandrel is introduced through an opening formed at one end of the tube below the plug, in particular in the axis of the internal canal of the tube.

The present invention also relates to a monocanalicular and/or monocaniculonasal intubation assembly comprising a mandrel made of a first substantially rigid material and a tube made of a second material that is less rigid than the first material, and essentially flexible, and a plug projecting laterally from the tube, preferably at one end of the latter, intended to lock the tube in position in a lachrymal canal, characterised in that the mandrel made from the first material has a greater length than the length of the tube and a part of the mandrel is inserted inside the tube, in particular such that one of its ends comes into contact with the closed end of the tube remote from the plug.

According to a preferred embodiment of the invention, the mandrel has a greater thickness in a direction perpendicular to the direction of its longitudinal extension, and in particular has a transverse cross sectional diameter which is between 0.3 mm and 0.5 mm. This is substantially lower than the dimensions of mandrels commonly used in the prior art.

According to a preferred embodiment of the invention the longitudinal extension of the silicone tube is between 15 mm and 60 mm, in particular is 35 mm.

The present invention also relates to a method in which a surgeon introduces into the lachrymal duct, from the side of the eye, an assembly according to the invention, the mandrel being enveloped in part by the tube from the side introduced, the introduction being performed until the plug comes into position at the lachrymal meatus to lock the tube in position, the mandrel and the tube then being arranged in the lachrymal passages, then the mandrel is extracted by removing it from the same eye side through which it was introduced.

By way of the example, a preferred embodiment of the invention is now described with reference to the drawings in which:

FIG. 1 is perspective view of an assembly according to the invention;

FIG. 2 is a transverse cross sectional view of a first embodiment of a tube of a monocanalicular intubation assembly according to the invention;

FIG. 3 is a longitudinal cross sectional view of a second embodiment of a tube of a monocanalicular intubation assembly according to the invention;

FIG. 3' is a view from above of the embodiment of FIG. 3; and

FIG. 4 is a cross section of section 20 of the tube of FIGS. 2, 3 and 3'.

FIG. 1 shows in perspective view, a monocanalicular and/or monocanaliculonasal intubation assembly according to the invention. The latter is formed, on the one hand, by a blind silicone tube 1 and, on the other hand, by a metal mandrel 2. The mandrel 2 has a longitudinal extension which is greater than the longitudinal extension of the tube 1, in particular 2 to 4 times greater. The mandrel 1 is inserted into the tube 2, such that its blind distal end 3 is substantially in contact with the interior wall of the tube 1 at the distal end 4 of the latter. The silicone tube 1 comprises, remote from its distal end 4, and in particular substantially at its proximal end 5 a plug 6. Said plug 6 is formed by a shank or neck 7 and by a collar 8 projecting laterally from the neck 7 at one end of the latter. The neck 7 extends in a longitudinal axis 9, which is substantially perpendicular to the longitudinal axis of the tube 10.

The proximal end 5 of the tube 1 is open (opening 13).

The tube 1 comprises a section 20 which extends between its proximal end 5 and the shank 7 and which has a greater transverse cross section than the transverse cross section of the rest of the tube. In particular, in said section 20 the tube comprises extension parts 21 in the form of longitudinal ribs with a triangular cross section, which are in excess of the circular cross section of the tube.

The function of the plug 6 is as follows. Once the surgeon has introduced the tube 1 and the mandrel 2 assembly (that is with part of the mandrel enveloped by the tube) at the eye side end of the lachrymal passages, the surgeon follows the advance of the assembly in the lachrymal passages until the assembly pierces the obstruction formed in the lachrymal passages that needs to be pierced to allow the passage of tears afterwards, firstly around the tube 1 with the mandrel removed. The advance of the assembly is stopped when the plug 6 reaches the eye side end of the lachrymal passages and the collar 8 abuts against the lachrymal shoulder or meatus formed at the end of the lachrymal duct Moreover, the section 20 with a greater thickness, when pushed into the lachrymal passages locks the tube in position to prevent it being removed. This action of the section 20 has the effect of blocking the displacement of the tube in the opposite direction to the one in which the collar blocks the displacement of the tube.

The greatest transverse dimension, i.e. here in the case of a circular cylindrical mandrel the diameter, of the transverse cross section of the mandrel is 0.4 mm, and in particular is between 0.3 mm and 0.5 mm.

According to an embodiment shown in FIG. 2 the securing of the plug to the tube is achieved by the insertion of a tab 12 projecting from the lateral surface of the shank 7 of the plug and adapted by tightening adjustment in the tube with adhesion to the internal wall of the tube 1. Thus a hole 13 is formed in the lateral wall of the tube 1 to allow for the passage of the mandrel.

According to another embodiment shown in FIG. 3, the plug is made in one piece with the tube, for example by moulding, and the opening 13' which allows the introduction of the mandrel 2 is made in the proximal end 5 of the tube 1.

The invention claimed is:

1. Monocaniculonasal and/or monocanalicular intubation assembly for nasolachrymal imperforation, comprising a hollow tube made of a flexible material defining therein a longitudinal passage for receiving a mandrel for pushing said hollow tube into said lachrymal duct, and a blocking plug for locking the tube in position in the lachrymal duct, said tube including a hole for the inserting of said mandrel into the tube, said hole formed in a lateral wall of said tube opposite said plug; said plug including a cylindrical shank and a collar protruding laterally from the whole cylindrical shank at a free end thereof, wherein said hollow tube has a cross section of circular shape with a diameter that is constant along said tube from said cylindrical shank toward an opposed end of said tube, said cylindrical shank being inclined relative to said tube and extending itself directly from said tube.

2. Assembly according to claim 1, characterised in that the tube comprises between its proximal end and the shank of the plug a section with a larger cross section than the rest of the tube.

3. Assembly according to claim 1, characterised in that the hole is formed in the lateral wall of the tube between its distal end and the shank of the plug, preferably closer to the latter than the distal end.

4. Assembly according to claim 1, characterised in that the mandrel has a greater thickness in transverse cross section of between 0.3 mm and 0.5 mm.

5. Assembly according to claim 1, characterised in that the longitudinal extension of the tube made of silicone is between 15 mm and 60 mm.

6. Assembly according to claim 1, characterised in that the shank is circular cylindrical.

7. Assembly according to claim 1, characterised in that the hole is formed by a slot which is collapsible.

8. Assembly according to claim 1, characterised in that the closed tube is all in one piece to its distal end.

9. Assembly according to claim 1, wherein said flexible material is silicone.

10. Monocaniculonasal and/or monocanalicular intubation assembly for nasolachrymal imperforation, comprising a hollow tube made of a flexible material defining therein a longitudinal passage for receiving a mandrel for pushing said hollow tube into said lachrymal duct, and a blocking plug for locking the tube in position in a lachrymal duct, said tube including a hole for the inserting of said mandrel into the tube, said hole formed in a lateral wall of said tube opposite said plug; said plug including a cylindrical shank and a collar protruding laterally from the cylindrical shank at a free end thereof, wherein said hollow tube has a cross section of circular shape with a diameter that is constant along said tube from said cylindrical shank toward a distal end of said tube, said cylindrical shank being inclined relative to said tube and extending itself directly from said tube, said tube including a supplementary section having a greater transverse cross section than the rest of the tube, said supplementary section extending from said plug in a direction opposite said opposed end.

11. Assembly according to claim 10, characterised in that the hole is formed in the lateral wall of the tube between its distal end and the shank of the plug, preferably closer to the latter than the distal end.

12. Assembly according to claim 10, characterised in that the mandrel has a greater thickness in transverse cross section of between 0.3 mm and 0.5 mm.

13. Assembly according to claim 10, characterised in that the longitudinal extension of the tube made of silicone is between 15 mm and 60 mm.

14. Assembly according to claim 10, characterised in that the shank is circular cylindrical.

15. Assembly according to claim 10, characterised in that the hole is formed by a slot which is collapsible.

16. Assembly according to claim 10, characterised in that the closed tube is all in one piece to its distal end.

17. Assembly according to claim 10, wherein said flexible material is silicone.

* * * * *